United States Patent [19]

Sullivan et al.

[11] Patent Number: 4,497,324
[45] Date of Patent: Feb. 5, 1985

[54] TEMPERATURE MONITORING CATHETER

[75] Inventors: Michael D. Sullivan, Glendale; Robert L. Murtfeldt, Redondo Beach; Arthur R. Yelsey, Corona del Mar, all of Calif.

[73] Assignee: American Hospital Supply Corporation, Evanston, Ill.

[21] Appl. No.: 538,715

[22] Filed: Oct. 3, 1983

[51] Int. Cl.³ .............................................. A61B 10/00
[52] U.S. Cl. ...................................... 128/736; 604/96
[58] Field of Search ................... 128/736; 604/96, 103, 604/113, 114, 276, 280

[56] References Cited

U.S. PATENT DOCUMENTS

| 4,024,873 | 5/1977 | Antoshkiw et al. | 604/96 |
| 4,176,660 | 12/1979 | Mylrea et al. | 128/736 X |
| 4,259,960 | 4/1981 | Taylor | 604/96 |
| 4,263,921 | 4/1981 | Trugillo | 128/736 |
| 4,369,795 | 1/1983 | Bicher et al. | 128/736 |
| 4,413,633 | 11/1983 | Yanda | 128/736 |
| 4,419,095 | 12/1983 | Nebergall et al. | 604/96 |

OTHER PUBLICATIONS

Mon-A-Therm Catalog 4-81.
Lilly et al., "Urinary Bladder Temperature Monitoring", *Critical Care Med.*, vol. 8, No. IV, Dec. 1980, pp. 742–743.
Electromedics Brochure 5-82.
Vitalmetrics Brochure "Urotrack Plus".

*Primary Examiner*—Edward M. Coven
*Attorney, Agent, or Firm*—Roger A. Williams

[57] ABSTRACT

A temperature monitoring catheter which has an elongated shaft having a distal end and a proximal end and a wall portion defining a drainage lumen extending longitudinally therethrough. The wall portion can also define a longitudinally extending inflation lumen which extends therethrough. The drainage lumen opens at the proximal end of the shaft through a drainage eyelet. An elastic, inflatable sleeve portion can be bonded to and extend annularly around a portion of the proximal end of the shaft. The elastic, inflatable sleeve portion is in fluid communication with the inflation lumen so that it can be inflated for retaining the catheter in a patient's body. A temperature thermistor is imbedded in the wall of the shaft at the proximal end of the shaft. A bifilar electric wire coil, helically wound, is imbedded in the wall of the shaft and connected at one end to the temperature thermistor. The other end of the bifilar wire extends from the distal end of the shaft for providing a connection to a power source and to a temperature monitor.

21 Claims, 3 Drawing Figures

U.S. Patent  Feb. 5, 1985  4,497,324
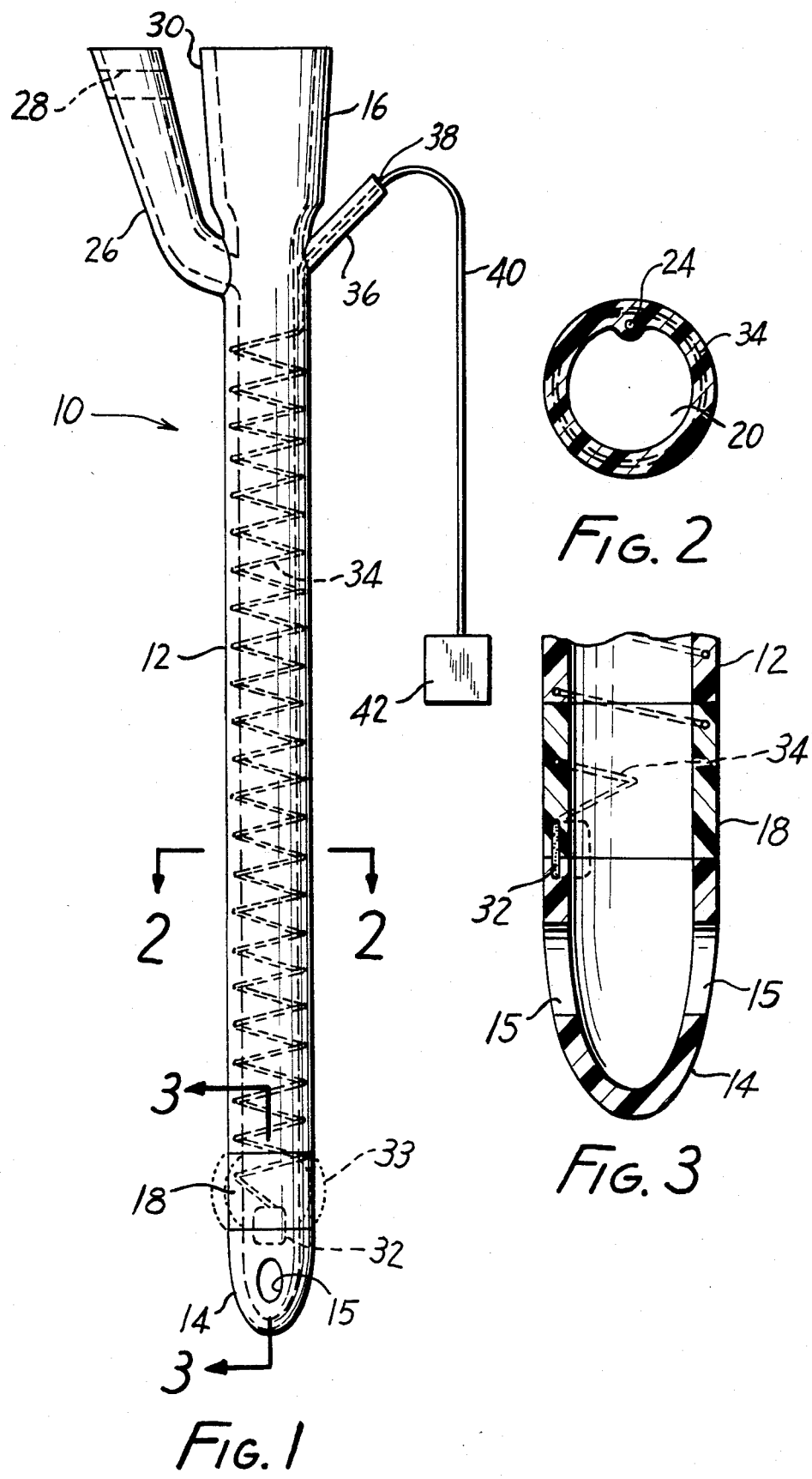

TEMPERATURE MONITORING CATHETER

BACKGROUND OF THE INVENTION

The invention herein relates to a catheter and more particularly to a catheter for draining fluid from a patient's body while simultaneously providing a monitoring of temperature of the patient. More particularly, the temperature monitoring catheter herein is directed to a temperature monitoring urological catheter which can be inserted in the urinary tract of a patient for draining urine from the bladder while simultaneously providing a monitoring of such patient's temperature.

Urinary catheters for draining urine from a patient's bladder have been used as a diagnostic aid for measuring the urine output of a patient. The measurement of urine output enables the determination of kidney viability of the infirmed patient.

Generally, there are two types of urinary catheters. Such catheters are either simple catheters or balloon retention catheters which are commonly referred to as Foley catheters. The simple catheters, commonly called urethral catheters, are used in patients wherein long indwelling times are not required. The balloon retention catheters include an inflation lumen which extends around the proximal end of the catheter, which lumen can be inflated after it is positioned within the patient's bladder to form an inflated balloon structure. The inflated balloon retains the proximal end of the catheter in the patient's bladder to insure drainage of any urine buildup from the bladder. The retention catheters, in addition to having an inflatable balloon section, include an inflation lumen which communicates with the inflatable balloon. The inflation lumen is provided with a valve which can be actuated to either introduce fluid to the balloon or to withdraw fluid from the balloon to enable removal of the catheter from the bladder.

Whether a simple catheter or a balloon retention catheter is utilized, urinary catheters include a drainage lumen which extends along and through the shaft of the catheter. The drainage lumen opens at the proximal end of the catheter shaft through a drainage eyelet or opening, which eyelet or opening is positioned within the patient's bladder. Urine which collects in the bladder flows through the eyelet along the drainage lumen and out of the catheter through the distal end. The distal end of the catheter is generally connected to a drainage bag for collecting the urine and providing a means for measuring the volume of urine collected.

There is available a three lumen, temperature monitoring, urinary catheter which is a balloon retention catheter. One of the lumens in the catheter is a drainage lumen and a second lumen in the catheter is the inflation lumen. The third lumen in the catheter provides a path for an electrical lead which extends axially along the shaft of the catheter to the proximal end where a temperature thermistor is positioned. The tri-lumen catheter thus provides for detecting temperature as well as draining urine from a patient's bladder. One disadvantage with such a tri-lumen catheter is that in order to provide for three lumens in a catheter having a fixed French size, the diameter of the drainage lumen is reduced. Thus, the rate of draining is reduced. Alternatively, to maintain a drainage rate, the diameter of the catheter shaft can be increased, thus increasing the diameter of the drainage lumen. Increasing the shaft diameter can cause greater discomfort for the patient and is undesirable.

Another drawback of such a tri-lumen catheter is that with normal and expected movement of a catheterized patient, the natural friction between the wire and catheter causes kinking of the wire within the third lumen. Such kinking can lead to breaking of the wire which potentially can erode through the catheter and lead to possible damage to the patient's urinary tract. The kinking can also bring about displacement of the thermistor or proximal end of the catheter. In addition, kinking of the wire in the catheter can cause some discomfort to the patient.

It would be desirable to provide a catheter which can be used for draining fluids from a patient while simultaneously providing temperature monitoring and which avoids the drawbacks of the presently available design.

SUMMARY OF THE INVENTION

The invention herein is directed to an improved temperature monitoring catheter. In particular, the temperature monitoring catheter herein provides a temperature detecting element at the proximal end of the catheter and an electrical wire connection extending through the shaft of the catheter which avoids kinking upon natural movements of the patient in which it is inserted.

The temperature monitoring catheter herein includes an elongated shaft having a distal end and a proximal end and a wall portion. The wall portion defines a drainage lumen extending longitudinally through the shaft, which drainage lumen opens through the wall at the proximal end of the shaft. The catheter herein can be a balloon retention catheter and as such would include a second lumen, an inflation lumen, also extending longitudinally through the shaft. In such a retention catheter, an elastic, inflatable sleeve portion is bonded to the outer surface of the wall and extends around a portion of the proximal end of the shaft. The inflatable sleeve portion provides a balloon element which can be inflated to form an inflated balloon for retaining the catheter in a patient's bladder. The elastic, inflatable sleeve portion is in fluid communication with the inflation lumen through an inflation opening extending through the wall of the shaft.

A temperature transducer capable of detecting temperature and converting the detected temperature to an electrical signal is imbedded in the wall at the proximal end of the shaft. The temperature transducer can be positioned such that at least a portion of the transducer is proximally positioned with regard to the elastic, inflatable sleeve. The temperature transducer is connected to an electrical lead which comprises a two strand electric wire coil helically wound and imbedded in the wall of the shaft of the catheter. One end of the electrical lead is connected to the temperature transducer at the proximal end of the catheter and the other end of the electrical wire lead extends from the catheter at the distal end to provide for connection to a temperature monitor which can convert the electric signals into a display of the temperature determined by the temperature transducer at the proximal end of the catheter.

BRIEF DESCRIPTION OF THE DRAWINGS

The temperature monitoring catheter herein will be described with regard to the accompanying drawings wherein:

FIG. 1 is a side elevational view of a temperature monitoring catheter herein;

FIG. 2 is a cross-sectional view of the temperature monitoring catheter of FIG. 1 taken along lines 2—2; and FIG. 3 is an enlarged sectional view of the proximal end of the temperature monitoring catheter shown in FIG. 1 taken along lines 3—3.

DESCRIPTION OF THE PREFERRED EMBODIMENT

The temperature monitoring catheter herein will be described with regard to the accompanying drawings. In addition, the catheter will be described in regard to a urinary catheter, although it will be appreciated by those having skill in the art that the invention herein can be utilized on catheters other than urinary catheters.

With regard to the drawings, a temperature monitoring catheter 10 is illustrated which has an elongated shaft 12, a proximal end 14 and a distal end 16. The terms "proximal" and "distal" are relative terms and are herein used in the medical sense whereby the proximal end will be regarded as the end closest to the patient's heart when the catheter is inserted in the patient's urinary tract.

The catheter shown in FIG. 1 is a balloon retention catheter and as such includes an annular elastic and inflatable sleeve 18 which is sealed to the shaft of the catheter. The catheter can be constructed from any suitable elastic material such as latex, silicone rubber, silicone coated latex, polyvinyl chloride, teflon, polyurethane, polyethylene, and the like.

Extending longitudinally through the shaft of the catheter is a drainage lumen 20. The drainage lumen 20 opens through a drainage eyelet 15 at the proximal end of the catheter and is open directly through the funnel 30 at the distal end of the catheter. The drainage lumen permits the flow of urine from the bladder through the drainage eyelet through the catheter to a collection receptacle such as a drainage bag which can be connected to the funnel.

In the balloon retention catheter shown in FIG. 1, there is a second lumen which is an inflation lumen 24. The inflation lumen extends longitudinally through the wall of the shaft and opens below the resilient sleeve 18 to provide fluid flow communication to the elastic sleeve. The inflation lumen extends from the catheter at the distal end through a side arm 26. The side arm is provided with a valve 28 which can be actuated by contact with the tip of a syringe (not shown) in order to permit passage of fluid through the valve. Fluid can be introduced through such a syringe connected to the valve and side arm, which fluid flows through the side arm, through the inflation lumen, and under the elastic sleeve 18 to inflate the sleeve and form an inflated balloon (shown in phantom as 33) at the proximal end of the catheter. The fluid can be withdrawn from the balloon by again connecting a syringe to the side arm and actuating the valve. The withdrawal of the fluid deflates the elastic sleeve, thus permitting withdrawal of the catheter from the bladder.

A temperature transducer 32 is imbedded in the wall of the shaft of the catheter at the proximal end. The temperature transducer detects temperature and converts the detected temperature to an electric signal. The temperature transducer can be a thermistor chip which is imbedded in the wall of the proximal end of the shaft. An acceptable thermistor chip is a chip exhibiting 2,252 ohms at 25° Centigrade. Such a chip does have applicability and can function as a temperature monitoring probe for use in catheters designed for use by humans for detecting their body temperature. The temperature transducer can be a thermistor chip having a resistance other than as in the preferred embodiment. For example, thermistor chips having resistances of 10,000 ohms, 50,000 ohms, 87,000 ohms at 25° C., and the like can also be used. The temperature transducer when used in combination with a retention catheter is imbedded in the wall of the shaft such that at least a portion of the temperature transducer extends proximally beyond the inflatable elastic sleeve 18. The temperature transducer can be positioned such that it lies completely proximal to the elastic sleeve. It is preferred that the temperature transducer be positioned distal to the drainage eyelet 15 in order to insure that the temperature transducer contracts a volume of urine whether such urine is flowing through the drainage lumen or present in the bladder of a patient.

An electrical lead 34 is helically coiled and imbedded in the wall of the shaft of the catheter. The electrical lead is a double-stranded wire which can provide power to the temperature transducer and transfer electric signals from the transducer. Any bifilar wire is acceptable and the strands of wire can be side by side or braided. The strands of wire can be of any gauge depending upon the thickness of the wall of the catheter shaft, but are preferably of a gauge from about 34 to about 44 in order to maximize the dimensions of the drainage lumen for optimum performance. A preferred bifilar wire is a bifilar copper wire wherein the wires are side by side with each wire separately insulated and each is a 36 gauge wire. The coiled bifilar wire 34 can be wire other than copper wire, for example, the bifilar wires can be constructed of nickel, tin plated copper, silver plated copper, aluminum, silver, platinum, gold and the like. The wires are attached at one end to the temperature transducer and the remaining end extends from the body of the catheter at the distal end of the catheter. The wire can extend through the wall and project outwardly from the shaft at the distal end or such wire can be encapsulated in a second side arm 36 which extends from the body of the catheter. In such a second side arm 36, the wires can be connected to an electrical connector 38 which can provide ease of connection to a lead wire 40 which leads to a temperature monitor for displaying the temperature sensed by the temperature transducer. The electrical lead 34 is coiled through the wall of the catheter shaft in order to prevent kinking of the wire. The coiled electrical lead 34 has a coil structure through the wall of about 5 to about 165 turns per linear inch of the shaft. The coiling of the wire permits the wire to move with the wall or body of the catheter as the patient moves. The coiled configuration prevents undue forces being exerted on the connection between the wire 34 ad the lead wire 40.

The preferred embodiment of the catheter herein is a latex catheter which is preferably formed by a dipping technique. In constructing the latex temperature monitoring catheter, a first mandrel representing the drainage lumen is dipped into a latex slurry. The first mandrel assembly can include a second spaced apart mandrel for forming the inflation lumen. After dipping the mandrel or mandrels into a latex slurry, the slurry coated mandrels are dried to form a coating of latex on the mandrels. The mandrels are then moved together whereby they are separated by the respective coatings on the mandrels which would be in contact but for the latex coatings. The electrical lead 34 is then wrapped around the two mandrels in the coiled helix fashion. Generally, approximately six foot of wire is used for each catheter, which is approximately 14 to 18 inches long. The wrapped mandrels are again dipped into a latex slurry to provide a coating covering the electrical wire and dried.

Although the temperature monitoring catheter herein has been described with regard to a urinary or Foley catheter, other catheters can be constructed such as interperitoneal, intercardial, respiratory, intervascular catheters, and the like.

We claim:

1. A temperature monitoring catheter, comprising:
   an elongated shaft having a distal end, a proximal end and a wall portion defining a drainage lumen extending longitudinally through the shaft and opening through a drainage opening at the proximal end of the shaft;
   temperature sensing means for determining temperature and converting such determined temperature to an electric signal, imbedded in the wall at the proximal end of the shaft; and
   a bifilar electrical wire coil helically extending around the drainage lumen and imbedded in the wall of the shaft, connected at one end to the temperature sensing means and providing an end extending from the shaft at the distal end of the shaft for connecting to a power source and a temperature monitor.

2. A temperature monitoring catheter as recited in claim 1 wherein the bifilar wire comprises a gauge from about 34 to about 44.

3. A temperature monitoring catheter as recited in claim 1 wherein the bifilar wire comprises an insulated bifilar copper wire.

4. A temperature monitoring catheter as recited in claim 1 wherein the wire coil comprises about 5 to about 165 turns per linear inch of catheter shaft.

5. A temperature monitoring catheter as recited in claim 1 wherein the temperature sensing means comprises a temperature sensitive thermistor.

6. A temperature monitoring catheter as recited in claim 5 wherein the thermistor comprises a thermistor exhibiting 2,252 ohms at 25° C.

7. A temperature monitoring catheter as recited in claim 1 further comprising an outwardly projecting side arm at the distal end of the shaft of the catheter through which a portion of the bifilar wire extends.

8. A temperature monitoring catheter as recited in claim 7 further comprising an electrical connector attached to the end of the bifilar wire at such outwardly projecting side arm, which connector provides means for connecting such bifilar wire to an electrical lead wire.

9. A temperature monitoring catheter as recited in claim 1 further comprising an elastic, inflatable sleeve portion bonded to and extending around a portion of the proximal end of the shaft of the catheter and an inflation lumen extending longitudinally through the wall of the shaft of the catheter which is in fluid flow communication with the elastic, inflatable sleeve portion to provide inflation of the sleeve portion and wherein at least a portion of the temperature sensing means is provided proximal to the elastic, inflatable sleeve portion.

10. A temperature monitoring catheter as recited in claim 9 wherein the temperature sensing means is provided proximal to the elastic inflatable sleeve portion.

11. A temperature monitoring catheter, comprising:
    an elongated shaft having a distal end, a proximal end and a wall portion defining a drainage lumen extending longitudinally through the shaft and opening through a drainage opening to the outside of the shaft at the proximal end and defining an inflation lumen extending longitudinally through the shaft;
    an elastic, inflatable sleeve portion bonded to and extending annularly around a portion of the proximal end of the shaft, which elastic, inflatable sleeve portion is in fluid communication with the inflation lumen;
    temperature sensing means for determining temperature and converting such determined temperature to an electric signal, which temperature sensing means is imbedded in the wall at the proximal end of the shaft; and
    a bifilar electric wire coil helically wound around the drainage lumen and imbedded in the wall of the shaft, connected at an end to the temperature sensing means and providing an end extending from the shaft at the distal end of the shaft for connecting to a power source and a temperature monitor.

12. A temperature monitoring catheter as recited in recited in claim 11 wherein the bifilar wire comprises a gauge from about 34 to about 44.

13. A temperature monitoring catheter as recited in claim 11 wherein the bifilar wire comprises an insulated bifilar copper wire.

14. A temperature monitoring catheter as recited in claim 11 wherein the wire coil comprises about 5 to about 165 turns per linear inch of catheter shaft.

15. A temperature monitoring catheter as recited in claim 11 wherein the temperature sensing means comprises a temperature sensitive thermistor.

16. A temperature monitoring catheter as recited in claim 15 wherein the temperature sensitive thermistor comprises a thermistor having a resistance of 2,252 ohms at 25° C.

17. A temperature monitoring catheter as recited in claim 11 wherein at least a portion of the temperature sensing means is located proximal to the elastic, inflatable sleeve portion.

18. A temperature monitoring catheter as recited in claim 11 wherein the temperature sensing means is located proximal to the elastic, inflatable sleeve portion.

19. A temperature monitoring catheter as recited in claim 11 further comprising an outwardly extending side arm at the distal end of the shaft through which a portion of the wire extends.

20. A temperature monitoring catheter as recited in claim 19 further comprising an electrical connector attached to the end of the wire at such outwardly extending side arm.

21. A temperature monitoring catheter as recited in claim 11 further comprising a second outwardly extending side arm at the distal end of the shaft through which the inflation lumen extends and in which is positioned a valve.

* * * * *